US010792175B2

(12) United States Patent
Gicquel et al.

(10) Patent No.: US 10,792,175 B2
(45) Date of Patent: Oct. 6, 2020

(54) ERGONOMIC PROTECTIVE SHELL DEVICE OF THE PERINEAL ORTHOSIS TYPE

(71) Applicant: CLARIPHARM, Saint Alban (FR)

(72) Inventors: Loic Gicquel, Montpellier (FR); Clarisse Lagadeuc, Pleneuf Val Andre (FR)

(73) Assignee: Claripharm, Saint Alban (FR)

( * ) Notice: Subject to any disclaimer, the term of this patent is extended or adjusted under 35 U.S.C. 154(b) by 559 days.

(21) Appl. No.: 14/769,039

(22) PCT Filed: Feb. 19, 2014

(86) PCT No.: PCT/FR2014/050344
§ 371 (c)(1),
(2) Date: Aug. 19, 2015

(87) PCT Pub. No.: WO2014/128405
PCT Pub. Date: Aug. 28, 2014

(65) Prior Publication Data
US 2016/0000594 A1 Jan. 7, 2016

(30) Foreign Application Priority Data

Feb. 20, 2013 (FR) ...................................... 13 51441
Jun. 5, 2013 (FR) ...................................... 13 55163

(51) Int. Cl.
*A61F 5/00* (2006.01)
*A61F 5/01* (2006.01)
(Continued)

(52) U.S. Cl.
CPC ............ *A61F 5/01* (2013.01); *A41D 13/0506* (2013.01); *A47C 7/029* (2018.08); *A61F 5/00* (2013.01);
(Continued)

(58) Field of Classification Search
CPC ... A41D 13/0525; A41D 1/084; A61F 5/0093; A61F 5/451; A61F 5/453; A61F 5/455; A61F 15/004; A47C 7/029
(Continued)

(56) References Cited

U.S. PATENT DOCUMENTS 3,229,692 A * 1/1966 Creed .................... A41D 7/005
2/466
4,186,739 A 2/1980 Hall et al.
(Continued)

FOREIGN PATENT DOCUMENTS

| CN | 201 127 648 Y | 10/2008 |
| EP | 0 448 336 A1 | 9/1991 |
| EP | 2 191 746 A1 | 6/2010 |

*Primary Examiner* — Keri J Nelson
*Assistant Examiner* — Adam Baker
(74) *Attorney, Agent, or Firm* — Craft Chu PLLC; Andrew W. Chu

(57) ABSTRACT

The ergonomic protective shell device of the orthosis type includes a structure provided with a front end and a rear end. The structure has a shape widening from the front end to the rear end and is symmetrical along a longitudinal vertical median plane. The structure includes at least one cavity extending from one to the other of the ends. The cavity follows the widening shape and includes a narrowing in the area of the widened rear end. There are rigid support zones formed in the area of the widened rear end on each side of the narrowing of the cavity.

8 Claims, 4 Drawing Sheets

(51) Int. Cl.
*A63B 71/12* (2006.01)
*A41D 13/05* (2006.01)
*A47C 7/02* (2006.01)
*A61F 5/058* (2006.01)

(52) U.S. Cl.
CPC ............ *A61F 5/0093* (2013.01); *A61F 5/058* (2013.01); *A63B 71/1216* (2013.01)

(58) Field of Classification Search
USPC .......................................................... 602/67
See application file for complete search history.

(56) References Cited

U.S. PATENT DOCUMENTS

| | | | | |
|---|---|---|---|---|
| 4,471,772 | A * | 9/1984 | Miller, Jr. ................. | A61F 5/41 |
| | | | | 2/403 |
| 5,479,942 | A * | 1/1996 | DiMatteo .................. | A61F 5/40 |
| | | | | 128/846 |
| 5,483,705 | A | 1/1996 | Dematteo | |
| 5,978,970 | A * | 11/1999 | Bright ..................... | A41D 1/084 |
| | | | | 2/227 |
| 7,712,156 | B2 * | 5/2010 | Raber .................... | A41D 1/088 |
| | | | | 2/403 |
| 2002/0124318 | A1 | 9/2002 | Loomos | |
| 2003/0079276 | A1* | 5/2003 | Forsyth .................. | A41D 1/084 |
| | | | | 2/267 |
| 2006/0229546 | A1 | 10/2006 | Littell | |
| 2008/0229486 | A1 | 9/2008 | Maier | |

* cited by examiner

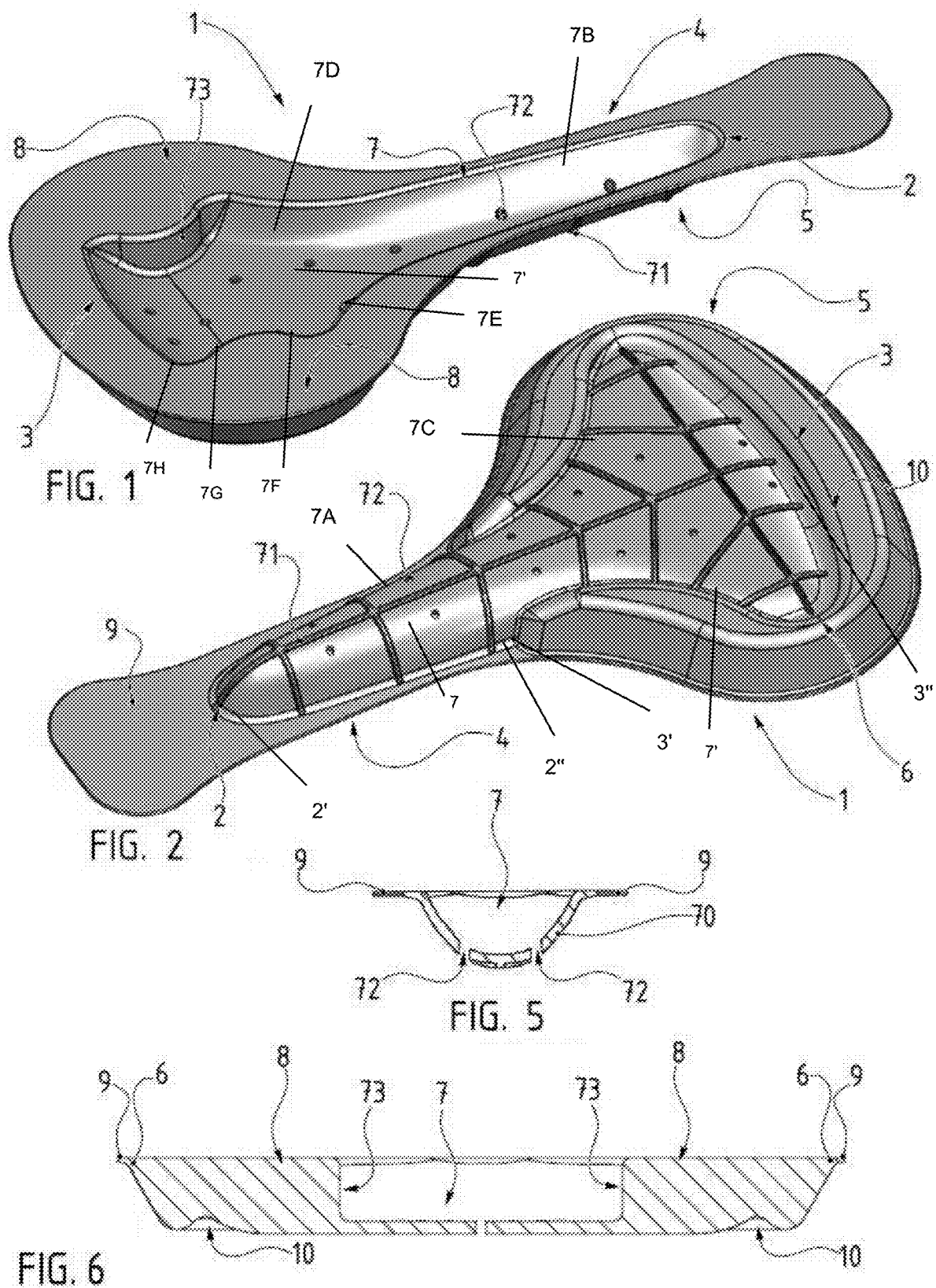

ERGONOMIC PROTECTIVE SHELL DEVICE OF THE PERINEAL ORTHOSIS TYPE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention is related to the medical and paramedical field for the prevention of pain and improving the comfort of a patient, preferably a female patient.

The invention will find a particular application within the framework of a patient, preferably a female patient, having undergone a medical procedure, namely a surgical procedure, suffering from pain in the crotch following such a procedure or due to a pathology.

In particular, but non-restrictively, the invention will be used with female patients at vaginal, anal and perineal level for preventing the pain induced by sutures, scars and wounds, as well as any other pain, namely induced by a tailbone dislocation or fracture.

According to alternative embodiments, the invention will be used with patients primarily, but non-restrictively, at anal level within a similar framework of prevention. The invention relates in particular to an ergonomic protective shell device of the orthosis type aimed at being placed at the level of the crotch of a patient, preferably of a female patient.

Many circumstances can cause pain in the crotch of a male patient or a female patient. For example, after giving birth, a woman may have received stitches after tearing of tissues or an episiotomy, but have vulvar or anal scuffing. In other cases, a female patient may suffer from hemorrhoids, hematomas and because of a dislocation of the coccyx. Such pain may also result from the treatment of perineal and vulvar condylomas, or may be caused due to an intervention on the perineum because of a bartholinitis, vulvar plasty or vaginal prolapse cures.

Though these pains are bearable in standing or lying statures, they become constraining and uneasily bearable when sitting, applying pressure on the sensitive areas. In some cases, these pressures are harmful to the good recovery of the male patient or the female patient, in particular the eventual healing of the tissues, and can even lead to complications or related pathologies, such as joint pain at the level of the during lactation, this malposition can also cause nipple cracks, a poor draining of the breasts, painful engorgement or mastitis.

2. Description of Related Art Including Information Disclosed Under 37 CFR 1.97 and 37 CFR 1.98

There is presently a precarious solution in the form of an inflatable cushion having an annular shape, leaving a central free space and providing a peripheral support on which the male patient or the female patient sits. Such a cushion is generally inflated in order to fill it with air. It is however not fully satisfactory, because of his lack of ergonomics, causing its displacement by sliding from the area to be protected. In addition, such a cushion regularly loses pressure and must be periodically re-inflated.

Finally, it is bulky and cumbersome, very impractical once it is in place.

SUMMARY OF THE INVENTION

The present invention provides an alternative that is aimed at coping with the disadvantages of the prior art by providing an ergonomic protective shell device of the orthosis type.

Such a shell has a shape capable of position it and hold it at the level of the crotch, while permitting to rest on anatomical areas away from the sensitive areas objects of potential pain.

In addition, its ergonomic nature is particularly adapted to the morphology of the male or female pelvis, whereby its dimensions can be adapted depending on the corpulence, the size and the sex of the person.

To this end, such a device is formed of a structure provided with a front end and a rear end, said structure having an increasingly widened shape from the front end to the rear end and symmetrical along a longitudinal vertical median plane. Furthermore, it is characterized in that said structure comprises at least one cavity extending from one to the other of said ends following said widened shape, and in that it comprises a narrowing at the level of the widened rear end, and in that said structure comprises rigid support areas provided for at the level of said rear widened rear end on both sides of said narrowing.

Thus, a male patient wearing or a female patient provided with the orthosis according to the invention can sit more comfortably, but also the transition to the sitting position is facilitated and made less painful.

In addition, according to further non-restrictive features, said support areas can be formed by a full thickness from the bottom of said cavity.

According to a preferred embodiment, said cavity may have a rounded bottom. Preferably, said cavity may comprise on the lower face a reinforcing mesh according to ridges projecting outwardly and intersecting with each other.

In particular, said cavity may include holes passing through its bottom and distributed over its length.

In addition, the generally concave shape of this orthosis forms a pan for recovering eventual body fluids and other secretions such as lochial discharges, permitting their guiding and their evacuation, namely through openings, whereby the latter can be located in front of the vagina in the female version of such an orthosis. According to one embodiment, the structure may comprise at least one peripheral contact fringe extending horizontally and projecting at least on part of the periphery on the upper surface of said structure.

According to another embodiment, said structure may be formed of a single element made of semi-rigid silicone-based material.

According to yet another embodiment, designed for men, said front end may comprise an opening.

Preferably, in this configuration for men, the structure may comprise, at the level of the front end, fastening means being in the form of at least one pair of strands extending in front, on both sides, of said cavity, said strands having connection means at their free end (103).

Therefore, the shape combined with a structure made of a specific material permits to provide a more rigid support zone than the rest of the orthosis, improving its application into contact with the body of the female patient and perfectly matching her morphology.

Further features and advantages of the invention will become clear from the following detailed description of non-restrictive embodiments of the invention, with reference to the attached figures.

BRIEF DESCRIPTION OF THE DRAWINGS

FIG. 1 represents a perspective view from a rear top view of a specific embodiment of an orthosis device according to the invention, such an orthosis being for a female patient.

FIG. 2 represents in perspective a front view from above of FIG. 1.

FIG. 5 represents a side view according to a vertical cross-section of FIG. 3 along an axis AA'.

FIG. 6 represents a side view according to a vertical cross-section of FIG. 3 along an axis BB'.

DETAILED DESCRIPTION OF THE DRAWINGS

Figures 3, 4:
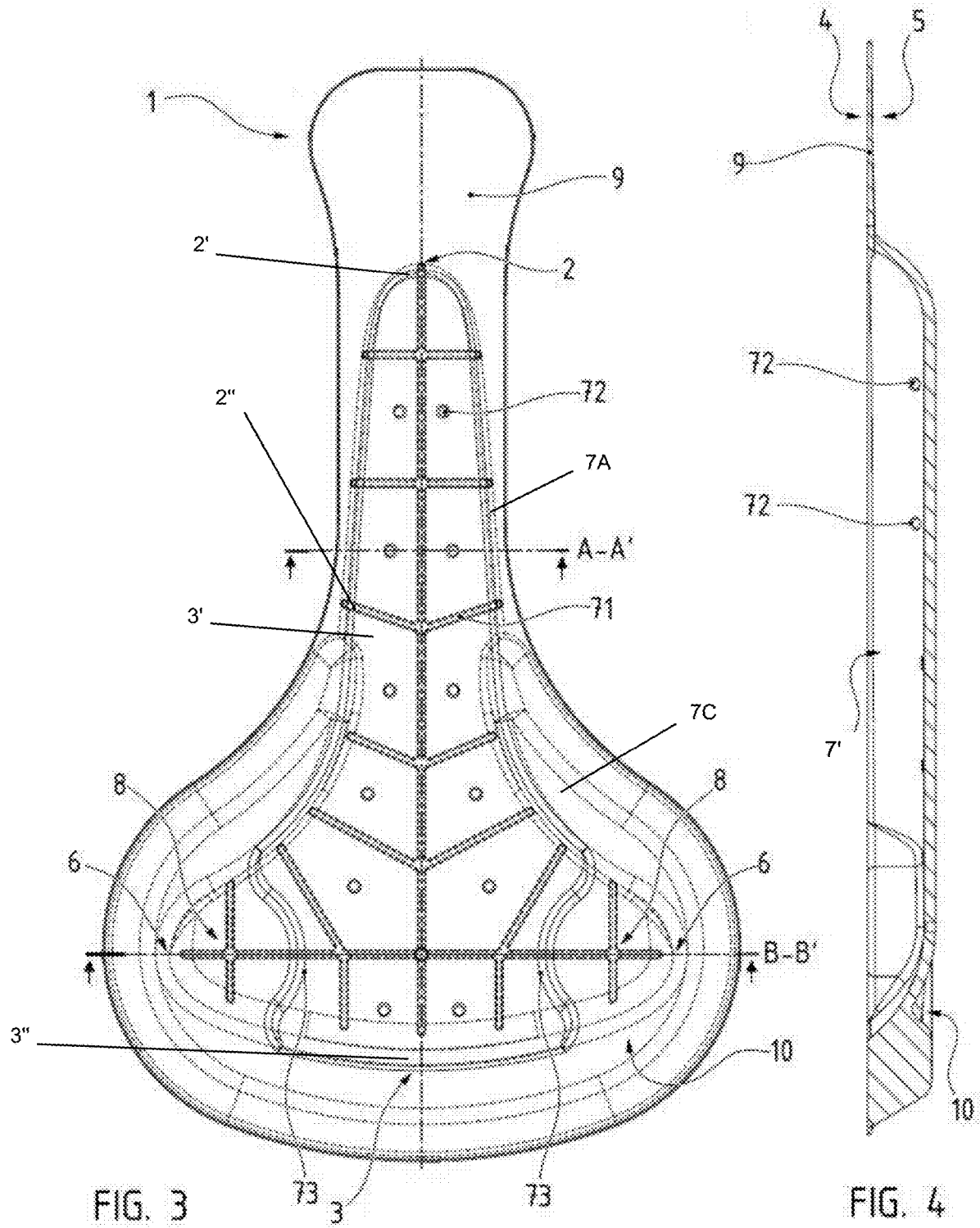
FIG. 3 represents a top plan view of a specific embodiment.
FIG. 4 represents a side elevation view according to a median longitudinal vertical cross-section of FIG. 3.
Figure 7:
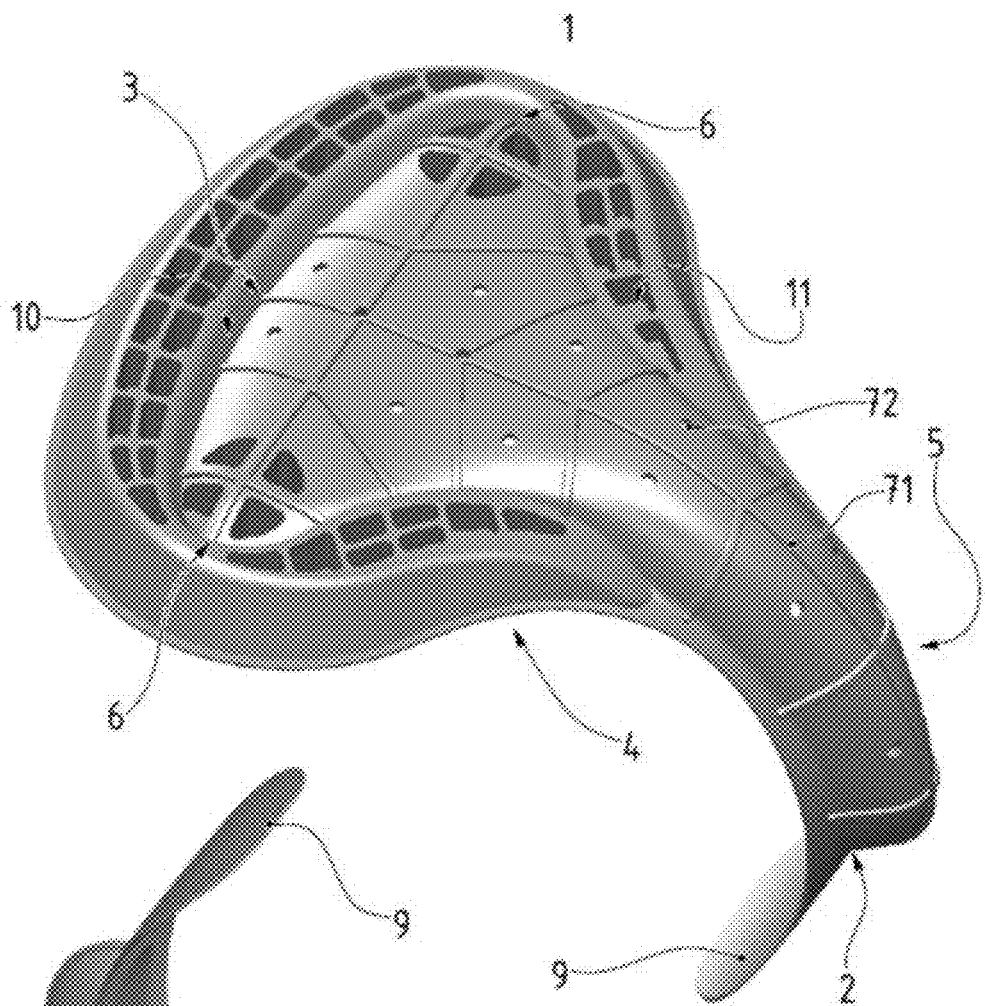
FIG. 7 represents a perspective bottom view of the preferred embodiment.

Referring to The present invention relates to an ergonomic protective shell device 1 of the orthosistype.

Such a device 1 is formed of a structure designed at least partially flexible and hollow, so as to be applied against the skin of a male patient or a female patient at the level of his or her crotch, deforming in order to conform to his or her anatomy, without therefore entering into contact with and resting on the painful areas induced by the above-mentioned reasons. In particular, the shape of the structure has a hollow central space, which, once the orthosis is in place, is located in front of the anatomical zone considered extending, for men, from the rear of the testicles until below the anus and, for women, from the vaginal opening to the anus, and prevents the contact and the resting at this level.

To this end, first of all said structure is provided with a front end 2, aimed at being positioned forwardly for men, behind the testicles, and for women at the level of the vagina or abdomen of the female patient, and a rear end 3 aimed at being positioned rearwardly at the level of the anus or the buttocks.

Moreover, said structure has an upper face 4 and a lower face 5, said upper face 4 being aimed at being applied against the skin when it is being placed.

In the first place, for women, as shown in FIGS. 1 to 9, this structure has an oblong and elongate general shape. More specifically, this shape is widened and increasing from the front end 2 to the rear end 3. In brief, the longitudinal walls extending laterally are spreading away from the front to the rear, the structure being wider at the latter place.

It should be noted that this widening can be rectilinear or substantially rectilinear along a front portion of the structure and curved, with an inflection or a larger extension at the level of the other portion located at the back. In addition, at the level of the latter and the rear end, the rear edge of the structure may also be rounded in the shape of an arc of a circle connecting two side ends located at the widest point of the widening.

Furthermore, this shape is symmetrical about a longitudinal vertical median plane.

An exemplary embodiment of such a shape is shown in FIG. 4.

Thus, said structure has then substantially and globally a shape of a cycle saddle, or of a rounded inverted T, coinciding with the human morphology at the level of the crotch and permitting to be positioned at that location.

Figure 9:
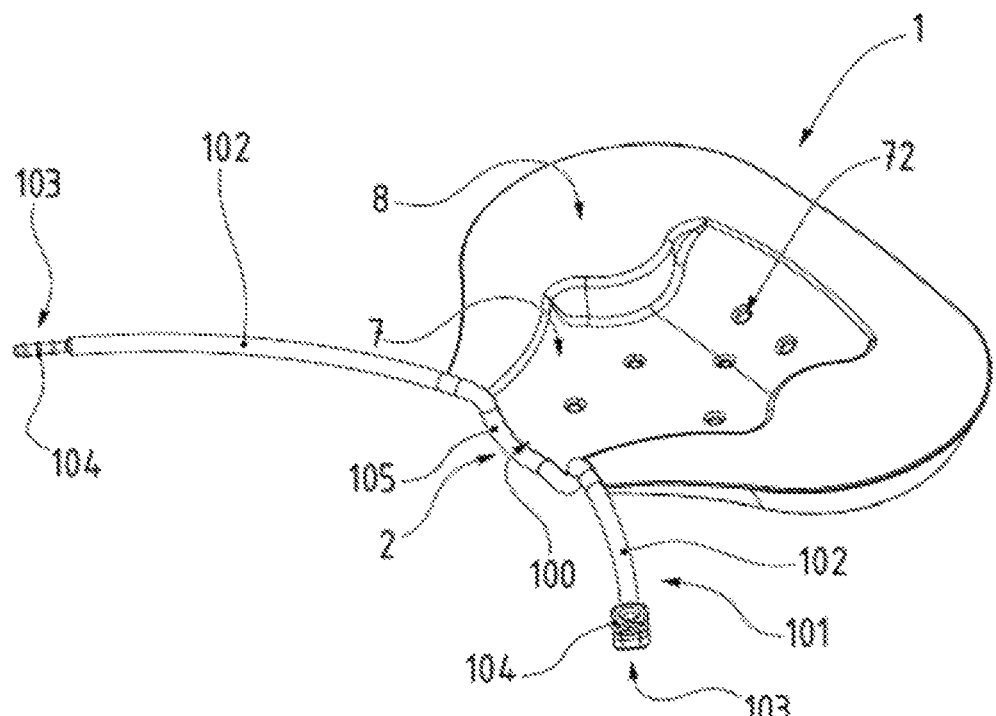
FIG. 9 represents another upper perspective view three-quarters from the front a top view of another embodiment of an orthosis for a male patient.
Figure 10:
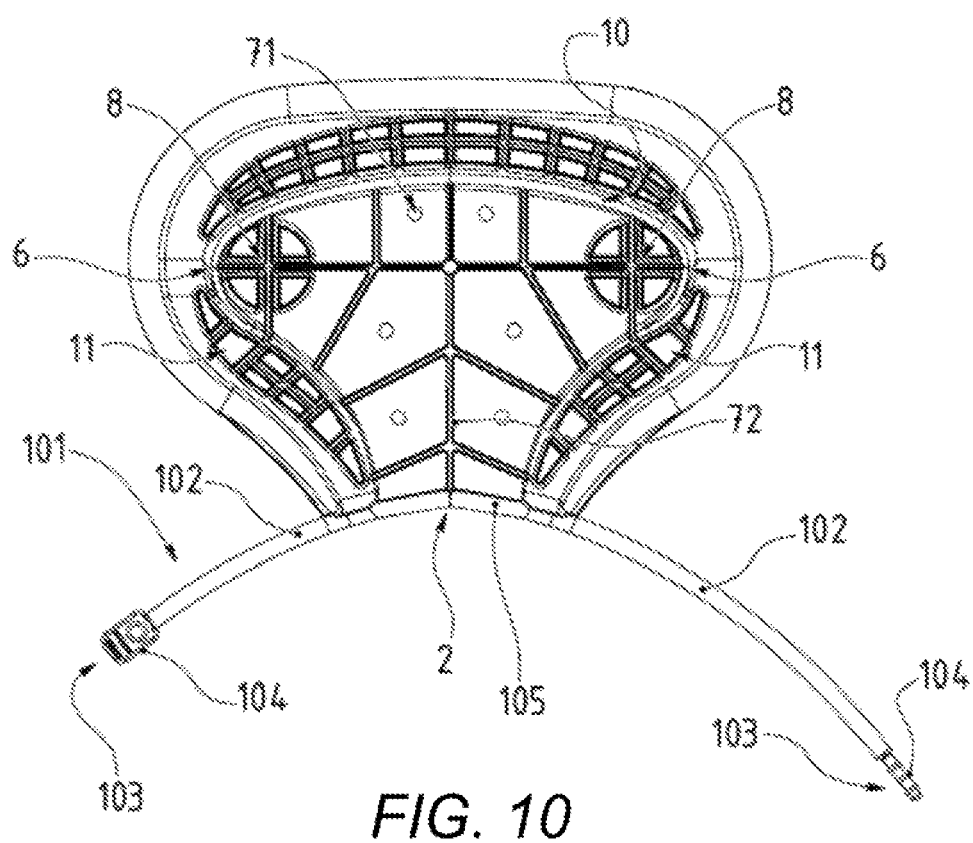
FIG. 10 represents a side elevation view from below of FIG. 9.

Furthermore, for men, as shown in FIGS. 9 and 10, the structure of the orthosis device 1 is shortened, not having an elongate, but a more compact shape. In other words, the front end 2 is not offset forwardly, but retracted backwardly, in order to coincide with the male genital anatomy.

Therefore, the widened shape of the structure of the orthosis for men increases more from this front end 2 to the rear end 3. In brief, the longitudinal walls extending laterally are spreading away from the front to the rear according to a larger initial angle, namely larger than 45° relative to the longitudinal median axis.

According to the embodiments shown in FIGS. 1 to 6 as well as 9 and 10, the structure is shown flat. According to another embodiment, shown in FIGS. 7 and 8, said structure may have an arcuate or curved shape, then a concave shape at its upper face 4, so as to match the rounded curvature of the anatomy.

According to an essential feature, said structure is designed hollow, so as not to be into contact with painful anatomical areas.

To this end, said structure has an upper face 4 and a lower surface 5 and comprises at least one cavity (the front cavity 7 made integral with the rear cavity 7') extending from one to the other of said front end or front end portion 2 having a front first end 2' and front second end 2", and a rear end portion 3 having a rear first end 3' and rear second end 3" along the said widened shape. In brief, the structure has, seen from above, concave walls providing at least one hollow space.

In particular, according to the preferred embodiment, in particular visible in FIGS. 1, 2 and 5, the front end portion 2 comprises lower surface front cavity walls 7A and upper face front cavity walls 7B so as to form the at least one front cavity 7 extending between the front end portion 2 and the rear end portion 3. The front cavity 7 is concave on the upper face 5. The rear end portion 3 comprises lower surface rear cavity walls 7C and upper face rear cavity walls 7D being adjacent and made integral with the lower surface front cavity walls 7A and the upper face front cavity walls 7B, respectively, so as to form the at least one rear cavity 7'. The front cavity 7 is widened on the lower surface 5 by the lower surface front cavity walls 7A from the front first end 2' to the front second end 2". The front cavity 7 is widened on the upper face 4 by the upper face front cavity walls 7B from the front first end 2' to the front second end 2". The rear cavity 7' is widened on the lower surface 5 by the lower surface rear cavity walls 7C from the rear first end 3' to the rear second end 3". The rear cavity 7' has a first rear widening 7E on the upper face by the upper face rear cavity walls 7D from the rear first end 3' toward the rear second end 3". The rear cavity 7' has a first rear narrowing 7F on the upper face 4 by the upper face rear cavity walls 7D from the first rear widening 7E toward the rear second end 3". The rear cavity 7' has a second rear widening 7G on the upper face 4 by the upper face rear cavity walls 7D from the first rear narrowing 7F to the rear second end 3". The first rear narrowing 7F on the upper face 4 and the second rear widening 7G on the upper face 4 by the upper face rear cavity walls 7D comprise support areas 8 on both sides of the rear cavity 7' on the upper face 4 between the first rear end 3' and the second rear end 3". The rear cavity 7' has a first rear narrowing on the upper face by the upper face rear cavity walls from the first rear widening toward the rear second end. The rear cavity 7' has a second rear narrowing 7H on the upper face 4 by the upper face rear cavity walls 7D from the support areas 8 toward the rear second end 3" on the upper face 4 so as to be aligned to receive anatomical areas located on both sides of a perineum. The structure has at the level of the cavity (the front cavity 7 and rear cavity 7') one single rounded wall 70 on the lower surface 5 formed by lower surface front cavity walls 7A and lower surface rear cavity walls 7C. In short, said cavity (the front cavity 7 are the rear cavity 7') has a rounded bottom on the lower surface 5. In addition, the bottom has a cross-section having the shape of an arc of a circle, of a more or less long chord depending on the place where it is located relative to the widening as a first rear widening 7E, conversely at the rear or at the front.

In addition, in the embodiment for men, said front end 2 may have an opening 100. The peripheral edge of the latter will then enter into contact with the rear surface of the scrotum, thus ensuring the closure of the cavity 7.

According to an alternative embodiment for men, not shown, the opening 100 of the front end 2 may be closed by a wall. The latter may be designed flexible and curved, having an ergonomic shape for entering into contact with the testicles, at the level of the rear surface of the scrotum.

In addition, in the embodiment for men, the structure of the device 1 comprises fastening means 101 for securing the orthosis and make it integral with the male anatomy. Preferably, these means 101 permit to secure the device 1 at the level of the base of the penis.

According to the preferred embodiment, the fastening means 101 are located at the level of the front end 2. In particular, they may be formed of at least one pair of strands 102 extending in front, on both sides, of the cavity 7, at the level of said opening 100. Such strands 102 may have a round or flattened cross-section, forming in the latter case straps. These strands 102 have at their free end 103 connecting means 104. The latter permit to fasten together said ends 103, then forming a closed loop.

Moreover, the connecting means 104 may be designed adjustable, in order to adjust the diameter of this loop, in particular to increase or to reduce the size of said loop, depending on the anatomy of the patient's penis.

According to the preferred embodiment, shown in FIGS. 9 and 10, said connecting means 104 may be formed, at the end 103 of a first strand 102, by a smaller hole, forming a female part of complementary shape and dimensions, which the end 103 of a second strand 102 is provided with.

Moreover, said smaller-diameter cross-section may be provided with a setback, namely of an annular shape, uniformly distributed over the length of the end 103 of said first strand 102. These rings permit to index positions by inserting them by force within said orifice of the female part of the second opposite strand 102, thus forming stops.

It should be noted that the strands 102 may form a bead 105 at the level and along the edge of the opening 100, improving the contact against the scrotum.

In addition, said strands 102 may preferentially be designed flexible. They can be made of the same material as the rest of the device 1.

According to an additional feature, for any orthosis device 1 for men or for women, as can be seen in FIG. 2, said cavity 7 can comprise on the lower face a reinforcing mesh according to ridges protruding outwardly and 71 intersecting with each other. In particular, a central ridge may extend along the median axis of symmetry, while others ridges join it while increasing their respective direction. Another transversal ridge may extend through the lateral ends 6.

In addition, the mesh permits to rigidify the structure of the device 1, while permitting its deformation.

In this respect, said structure is preferably formed of a single element made of a semi-rigid silicone-based material. In short, this material provides the orthosis with flexibility, elasticity and shape memory, permitting its distortion in order to be applied against and to match the anatomy, then to return into the original position, as shown in FIGS. 1 and 2, namely for its cleaning and storage.

Preferably, said material may be a biocompatible and microporous silicone.

Preferably, said silicone can be an antibacterial medical silicone.

Therefore, said mesh ensures that the shape of the structure is maintained despite the flexibility of the material it is made of, in particular in the case of silicone, which is a very flexible material. Thus, even when it is deformed and positioned at the level of the crotch, the structure maintains the hollow space of the cavity 7.

In this respect, the hollow space will permit to recover the eventual flows of body fluids, such as lochial discharges. In order to prevent these fluids from stagnating in the the one hand, the rounded shape of the cavity 7 permits to guide the flow towards the lower part. On the other hand, said cavity 7 may comprise holes 72 passing through its bottom, distributed over its length, preferably on both sides of the median plane of symmetry.

Advantageously, the device 1 is designed so as to provide support zones aimed at being positioned in front of two anatomical areas located on both sides of the perineum, between the anal opening and the vaginal opening, for women, or between the back of the scrotum, for men, at the level of the rear perineum and close to the ischial tuberosity.

To this end, said cavity comprises a narrowing at the level of the widened rear end 3. In short, at the widest rear area of the structure, the width of the cavity 7 is present a reduction, as shown in FIG. 6.

In particular, this reduction can be achieved through recesses 73. The latter may have a rounded, convex shape, as shown in FIG. 3.

This narrowing then permits to provide on both sides of the cavity 7 two thicker portions for receiving and supporting the aforementioned anatomical areas, without causing pressure at the level of the sensitive and painful areas of the perineum and the anus.

Thus, said structure comprises rigid support areas 8 provided for at the level of said widened rear end 3, on both sides of said narrowing.

In addition, said support zones 8 may be formed by a full thickness from the bottom of said cavity (the front cavity 7 and rear cavity 7'). In short, under the zones 8 the cavity (the front cavity 7 and rear cavity 7') is filled. This filling can be made with the same material as that forming the entire device 1, but also with a different material, for example a gel, providing resistance, but also flexibility. In the latter case, the different material is enclosed in a pocket formed between the sidewalls of the cavity (the front cavity 7 and rear cavity 7') including at the level of each recess 73, the top wall and the bottom wall of the structure.

According to another embodiment, said support zones 8 can be designed partially hollow, namely alveolar. These alveoli may namely be in the form of a honeycomb. In short, the inside of these zones 8 is hollow and braced by walls ensuring the desired rigidity. This inner ventilation also permits to reduce by at least 20 to 25% the weight of the device 1.

Figure 8:
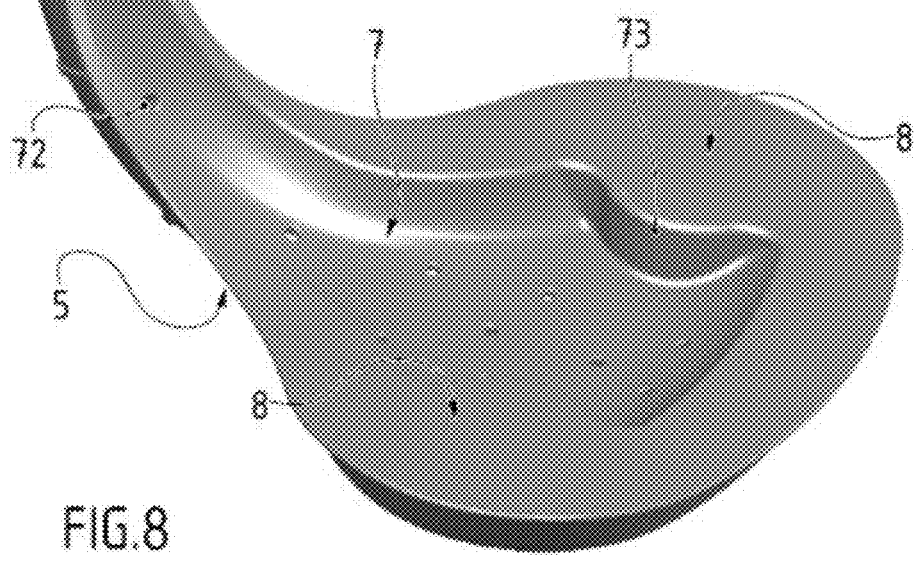
FIG. 8 represents an upper perspective view of FIG. 7.

According to the embodiment shown in FIG. 8, the thickness of the rest of the reinforcing mesh, limiting the deformation of the device 1 when it is in place, namely resting when the patient goes into a sitting position. Said alveoli 11 may be distributed around the support zones 8 and the concavity 7.

It should be noted that these alveoli 11 may be designed so as to end at the lower surface 5 of said device 1.

According to an additional feature, in order to improve the structure of the device 1 and to provide it with flexibility and maintaining the flexibility without unduly deforming in the unwanted configurations, said structure may comprise at the level of its rear portion at least one groove 10. The latter may extend at least partially around the rear portion of the structure, on both sides of the support areas 8. In addition, said groove 10 is provided for in the lower surface 5, in the form at least one recess having a globally inverted V-shape. Thus, the bottom of this groove 10 forms a ridge inside said structure, increasing its rigidity.

According to the embodiment shown in FIG. 2, the groove 10 comprises two ends located at the level of the widening of the rear portion of the structure. From these ends, the groove 10 diverges towards the rear, i.e. the width of its opening is increasing, then narrows until it join anew the levels of each side end 6. In addition, a portion of the groove 10 continues at the level of the rear end 3 of the structure, forming an arc oriented substantially orthogonally to the longitudinal median axis of the device 1. Finally, this groove portion spreads away from the ends 6, to the center at the level of said axis.

According to an additional feature, the preferred embodiment, shown in the figures, provides that the structure may comprise at least one peripheral contact fringe 9 extending horizontally projecting at least over a portion of the periphery on the upper surface of said structure. Such fringe ensures, on the one hand, a contact with the skin and the holding of the structure, namely by addition of an adhesive directly on the skin, and, on the other hand, the tightness of the device 1, preventing any flow from exiting the cavity 7.

In addition, this fringe may have a different width at different levels of the periphery of the structure, more elongated forwardly, substantially equivalent over the entire periphery of the widened rear portion, but less wide, to non-existent, at the level of the median or central portion. Indeed, the latter is aimed at being accommodated at the level of the inner thighs where space is more limited.

Thus, the device 1 according to the invention permits, thanks to the shape and constitution of the structure, a support located away from the sensitive and painful anatomical areas, while avoiding the contact with the latter arranged in front of the cavity 7, providing an orthosis improving the comfort and protecting said areas from any pressure.

We claim:

1. An ergonomic protective shell device of an orthosis type, the shell device comprising:
    a structure having an upper face and a lower surface and being comprised of a front end portion having a front first end and front second end and a rear end portion having a rear first end and a rear second end, said front second end being wider than said front first end, said rear second end being wider than said rear first end, said front second end being adjacent and made integral with said rear first end, said rear end portion being wider than said front end portion, said structure being symmetrical about a vertical longitudinal median plane,
    wherein said front end portion comprises lower surface front cavity walls and upper face front cavity walls so as to form a front cavity extending between said front end portion and said rear end portion and being concave on said upper face,
    wherein said rear end portion comprises lower surface rear cavity walls and upper face rear cavity walls being adjacent and made integral with said lower surface front cavity walls and said upper face front cavity walls, respectively, so as to form a rear cavity, the front cavity being made integral with the rear cavity,
    wherein the front cavity is widened on said lower surface by said lower surface front cavity walls from said front first end to said front second end,
    wherein the front cavity is widened on said upper face by said upper face front cavity walls from said front first end to said front second end,
    wherein the rear cavity is widened on said lower surface by said lower surface rear cavity walls from said rear first end to said rear second end,
    wherein the rear cavity has a first rear widening on said upper face by said upper face rear cavity walls from said rear first end toward said rear second end,
    wherein the rear cavity has a first rear narrowing on said upper face by said upper face rear cavity walls from said first rear widening toward said rear second end,
    wherein the rear cavity has a second rear widening on said upper face by said upper face rear cavity walls from said first rear narrowing to said rear second end,
    wherein said first rear narrowing on said upper face and said second rear widening on said upper face by said upper face rear cavity walls comprise support areas on both sides of the rear cavity on said upper face between said first rear end and said second rear end,
    and
    wherein the rear cavity has a second rear narrowing on said upper face by said upper face rear cavity walls from said first rear widening toward said rear second end, wherein the rear cavity has a second rear narrowing on said upper face by said upper face rear cavity walls from said support areas toward said rear second end on said upper face so as to be aligned to receive anatomical areas located on both sides of a perineum.

2. The shell device according to claim 1, wherein said support areas are comprised of a filled thickness from said upper face to said lower surface of the rear cavity.

3. The shell device according to claim 1, wherein the front cavity and the rear cavity have a rounded bottom made integral on said lower surface.

4. The shell device according to claim 1, further comprising:
    ridges projecting outwardly from said lower surface of the front cavity and the rear cavity, said ridges intersecting with each other; and
    a reinforcing mesh between said ridges.

5. The shell device according to claim 1, wherein the front cavity and the rear cavity comprise openings passing through a respective lower surface thereof, said openings being distributed over a length of the front cavity and the rear cavity.

6. The shell device according to claim 1, further comprising at least one peripheral contact fringe extending horizontally and projecting from said front first end of said front end portion.

7. The shell device according to claim 1, wherein said structure is comprised of a silicone-based material.

8. The shell device according to claim 1, wherein said upper surface has a shape selected from a group consisting of arcuate and curved.

\* \* \* \* \*